United States Patent [19]

Grassmé

[11] 4,013,036

[45] Mar. 22, 1977

[54] TIME SWITCH DEVICE FOR X-RAY DIAGNOSTIC APPARATUS

[75] Inventor: Ulrich Grassmé, Nuremberg, Germany

[73] Assignee: Siemens Aktiengesellschaft, Berlin & Munich, Germany

[22] Filed: Nov. 13, 1975

[21] Appl. No.: 631,612

[30] Foreign Application Priority Data

Dec. 23, 1974 Germany .......................... 2461263

[52] U.S. Cl. ............................ 116/129 T; 116/133
[51] Int. Cl.² .......................................... G09F 9/00
[58] Field of Search ........... 116/129 T, 133, 124 A, 116/DIG. 21; 250/322

[56] References Cited

UNITED STATES PATENTS

| | | | |
|---|---|---|---|
| 3,183,885 | 5/1965 | Venema | 116/133 X |
| 3,198,923 | 8/1965 | Tripp | 116/133 X |
| 3,301,212 | 1/1967 | Foster et al. | 116/133 X |

Primary Examiner—Jerry W. Myracle
Attorney, Agent, or Firm—Hill, Gross, Simpson, Van Santen, Steadman, Chiara & Simpson

[57] ABSTRACT

A time switch device for X-ray diagnostic apparatus, in particular for the preparation of tooth or dental exposures, including a knob for the setting of the exposure periods and which has a time scale on a scale carrier associated therewith. The knob has associated therewith a symbol carrier which, in the displacement direction of the knob, is adjustable relative to the knob and to the time scale, on which there are drawn the symbols of the objects which are to be X-rayed at such a spacing relative to each other whereby, upon the setting of one symbol on the exposure period associated therewith, the other symbols are then located opposite to the exposure periods which are associated therewith.

6 Claims, 1 Drawing Figure

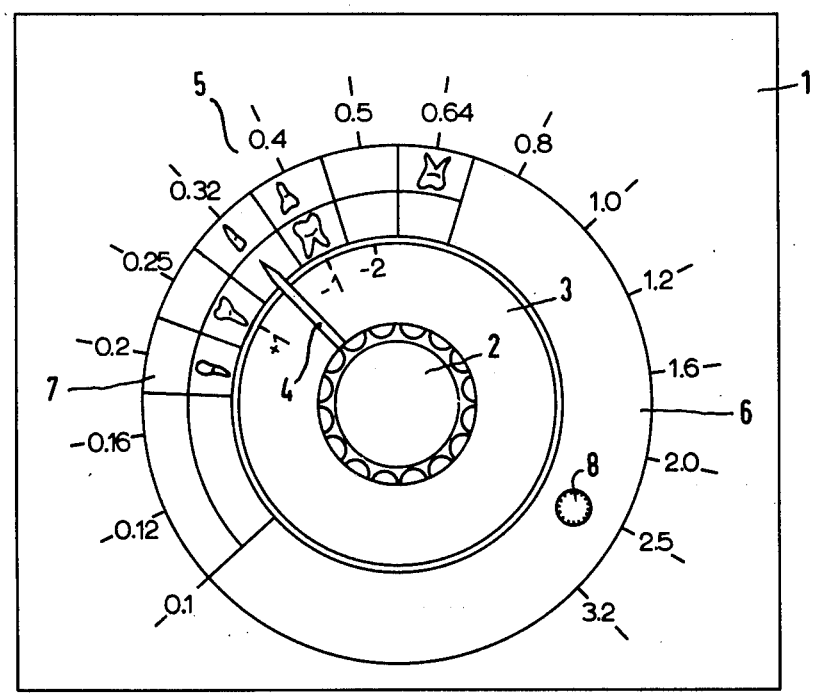

TIME SWITCH DEVICE FOR X-RAY DIAGNOSTIC APPARATUS

FIELD OF THE INVENTION

The present invention relates to a time switch device for X-ray diagnostic apparatus, in particular for the preparation of tooth or dental exposures, including a knob for the setting of the exposure periods and which has a time scale on a scale carrier associated therewith.

DISCUSSION OF THE PRIOR ART

In known time switches of this type the exposure period for the object which is to be X-rayed must be initially determined, in particular obtained by means of a table, and the rotary knob with a marker then set to this time. Thereafter, when an exposure of another object is to be prepared, then again the new exposure period must initially be determined and the rotary or turn knob set to the newly determined exposure period. The operation of the known time switches thereby becomes relatively cumbersome.

SUMMARY OF THE INVENTION

Accordingly, it is an object of the present invention to provide a time switch device of the above-mentioned type which has been improved with respect to the setting of the exposure data.

The foregoing object is inventively achieved in that the knob has associated therewith a symbol carrier which, in the displacement direction of the knob is adjustable relative to the knob and to the time scale, on which there are drawn the symbols of the objects which are to be X-rayed at such a spacing relative to each other whereby, upon setting of one symbol on the exposure period associated therewith, the other symbols are then located opposite to the exposure periods which are associated therewith. Pursuant to the invention it is thus merely necessary for the preparation of exposures to determine the exposure period for one of the objects on the symbol carrier, for example, on the basis of a table, and to then correspondingly adjust the symbol carrier. Through the intermediary of this setting the exposure periods for the other objects are then similarly determined, and the setting of the time switch for any of the objects which are drawn on the symbol carrier may be carried out in a simple manner in that the knob with one marker or index is set to this object.

A suitable further feature of the present invention resides in that the knob is provided with a correcting scale which permits the exposure periods to be correlated with the object thickness. In this instance, for a normally thick object, the knob is set with a zero marker on the current object symbol, whereas for an object which deviates from the normal thickness, the setting of the knob to that symbol is not carried out by means of the zero marker but by means of a correcting marker or index which deviates therefrom.

BRIEF DESCRIPTION OF THE DRAWING

Further advantages and details of the invention may now be ascertained from the following description of an exemplary embodiment, taken in conjunction with the single FIGURE of the accompanying drawing, showing a time switch device of the above-mentioned type.

DETAILED DESCRIPTION

Illustrated in the single FIGURE of the drawing is the housing 1 of a time switch for dental X-ray diagnostic apparatus, which supports a rotary or turn knob 2, the latter of which is fixedly connected with a correction scale carrier 3 and an indicator 4. On the housing 1, the exposure times which are provided for the individual types of teeth are fixedly drawn on a time scale 5. Interposed between the correction scale carrier 3 and the time scale 5 is a ring target or disc 6 serving as an object scale carrier located concentrically relative to the turn knob 2 and rotatable with respect to the latter and the housing 1, and which carries an object scale 7. Illustrated on the object scale 7, in two concentric scale regions representative of the upper and lower jaws are symbolically the three tooth types for which the exposure periods are to be set. The object scale carrier 6 is adapted to be rotated by means of a knob 8 about the axis of the turn knob 2, and lockable in position with respect to the housing 1. The securing may be effectuated, for example, in that the rotary knob 8 is screwed into the object carrier 6 and thereby has its end pressed against the housing 1.

The setting of the exposure periods is carried out by means of the illustrated time switch in such a manner in that, initially for one tooth type, for example the back teeth or molars of the upper jaw, the exposure period, for instance, is determined with the aid of a table. In the illustrated example this time period is 0.64 seconds. The symbol of this tooth is now set through rotation of the object scale carrier 6 opposite the corresponding exposure period. The other tooth symbols thus lie opposite the exposure periods associated therewith, so that a simple setting of the exposure data becomes possible in that the turn knob 2 with the indicator 4 is set to the respective tooth symbol. The indicator 4 is hereby correlated with the normal thickness of an object. If the object is thicker than normal, the turn knob 2 is not set to the respective tooth symbol by means of the indicator 4, but through the marker +1. If the object is thinner than normal, than the turn knob 2 is set to the respective object by means of marker −1 or −2. The scale on the correction scale carrier 3 in a simple manner also allows for a correlation of the set exposure periods to the object thickness.

The object scale carrier 6 must be displaced only relatively infrequently, inasmuch as the exposure periods which are associated with the individual exposure objects can be retained over lengthier time intervals. They vary, for example, when the film developer is to be exchanged or another film type is to be utilized.

While there has been shown what is considered to be the preferred embodiment of the invention, it will be obvious that modifications may be made which come within the scope of the disclosure of the specification.

What is claimed is:

1. In a time switch device for X-ray diagnostic apparatus, particularly for the preparation of tooth exposures; including a knob for the setting of the exposure periods; and a scale carrier having a time scale thereon being associated with said knob, the improvement comprising: a symbol carrier being associated with said knob and being displaceable in the setting direction of said knob relative to said knob and to said time scale; and symbols of the objects to be X-rayed being provided on said symbol carrier at such a spacing relative to each other whereby, upon setting one said symbol to the exposure period associated therewith, the other symbols will be located opposite their respectively associated exposure periods on the time scale.

2. A time switch device as claimed in claim 1, said knob comprising a turn knob, said time scale and said symbol carrier being concentrically arranged relative to said turn knob.

3. A time switch device as claimed in claim 2, said symbol carrier being a target ring.

4. A time switch device as claimed in claim 1, said symbol carrier being lockable in position relative to the housing of said time switch device.

5. A time switch device as claimed in claim 1, said symbol carrier including two scale areas containing tooth symbols for the teeth of, respectively, the upper jaw and the lower jaw.

6. A time switch device as claimed in claim 1, comprising a correction scale on said knob for correlating the set exposure times to the object thickness.

* * * * *